United States Patent [19]

Bosslet et al.

[11] Patent Number: 5,710,134
[45] Date of Patent: Jan. 20, 1998

[54] COMBINATION OF NECROSIS-INDUCING SUBSTANCES WITH SUBSTANCES WHICH ARE ACTIVATED BY NECROSES FOR THE SELECTIVE THERAPY OF TUMORS AND INFLAMMATORY DISORDERS

[75] Inventors: Klaus Bosslet; Jörg Czech, both of Marburg; Dieter Hoffmann, Marburg-Elnhausen, all of Germany

[73] Assignee: Behringwerke Aktiengesellschaft, Marburg, Germany

[21] Appl. No.: 446,211

[22] Filed: May 19, 1995

[30] Foreign Application Priority Data

May 20, 1994 [DE] Germany .......................... 44 17 865.4

[51] Int. Cl.$^6$ .................................................. A61K 31/70
[52] U.S. Cl. .................................................. 514/34; 536/6.4
[58] Field of Search .................................. 514/34; 536/6.4

[56] References Cited

U.S. PATENT DOCUMENTS

| | | | |
|---|---|---|---|
| 3,590,028 | 6/1971 | Arcamone et al. | 260/210 |
| 4,012,448 | 3/1977 | Smith et al. | 260/210 |
| 4,874,780 | 10/1989 | Borretzen et al. | 514/452 |
| 5,219,739 | 6/1993 | Tischer et al. | 435/69.4 |

FOREIGN PATENT DOCUMENTS

| | | | |
|---|---|---|---|
| 511917 | 11/1992 | European Pat. Off. | 260/210 |
| 4236237 | 4/1994 | Germany | 260/210 |

OTHER PUBLICATIONS

Senter et al., "Generation of Cytotoxic Agents By Targeted Enzymes", *Bioconjugate Chem.*, vol. 4:3–9, (1993).
Terman et al., "Identification of a New Endothelial Cell Growth Factor Receptor Tyrosine Kinase", *Oncogene*, vol. 6:1677–1683, (1991).
Ullrich et al., "Signal Tansduction by Receptors With Tyrosine Kinase Activity", *Cell*, vol. 61:203–212, (1990).
Millauer et al., "High Affinity VEGF Binding and Developmental Expression Suggest Flk-1 As A Major Regulator of Vasculogenesis and Angiogenesis", *Cell*, vol. 72:835–846, (1993).
Millauer et al., "Glioblastoma Growth Inhibited in vivo By A Dominant-Negative Flk-1 Mutant", *Nature*, vol. 367:576–579, (1994).
Kaipainen et al., "The Related FLT4, FLT1, and KDR Receptor Tyrosine Dinases Show Distinct Expression Patterns in Human Fetal Endothelial Cells", *J. Exp. Med.*, vol. 178:2077–2088, (1993).
Plate et al., "Up-Regulation Of Vascular Endothelial Growth Factor And Its Cognate Receptors In A Rat Glioma Model Of Tumor Angiogenesis", *Cancer Research*, vol. 53:5822–5827, (1993).

Clarke et al., "The Identification Of Proliferation And Tumour-Induced Proteins In Human Endothelial Cells: A Possible Target For Tumour Therapy", *Electrophoresis*, vol. 12:500–508, (1991).
Hagemeier et al., "A Monoclonal Antibody Reacting With Endothelial Cells Of Budding Vessels In Tumors And Inflammatory Tissues, And Non–Reactive With Normal Adult Tissues", *Int. J. Cancer*, vol. 38:481–488, (1986).
Brooks et al., "Requirement of Vascular Integrin $\alpha_v\beta_3$ For Angiogenesis", *Science*, vol. 264:569–571, (1994).
Brooks et al., "Integrin $\alpha_v\beta_3$ Antagonists Promote Tumor Regression By Inducing Apoptosis Of Angiogenic Blood Vessels", *Cell*, vol. 79:1157–1164, (1994).
Terman et al., "Identifiacation Of The KDR Tyrosine Kinase As A Receptor For Vascular Endothelial Cell Growth Factor", *Biochemical And Biophysical Research Communications*, vol. 187, No. 3, pp. 1579–1586, (1992).
Carnemolla et al., "A Tumor–Associated Fibronectin Isoform Generated By Alternative Splicing OF Messenger RNA Precursors", *The Journal of Cell Biology*, vol. 108:1139–1148, (1989).
Castellani et al., "The Fibronectin Isoform Containing The ED–B Oncofetal Domain: A Marker Of Angiogenesis", *Int. J. Cancer*, vol. 59:612–618, (1994).
Fernandez–Ruiz et al., "Assignment of The Human Endoglin Gene (END) to 9q34→qter", *Cytogenet Cell Genet*, vol. 64:204–207, (1993).
Gougos et al., "Primary Structure Of Endoglin, An RGD–Containing Glycoprotein Of Human Endothelial Cells", *The Journal of Biological Chemistry*, vol. 265, No. 15, pp. 8361–8364, (1990).
Wang et al., "A Monoclonal Antibody Detects Heterogeneity In Vascular Endothelium Of Tumours And Normal Tissues", *Int. J. Cancer*, vol. 54:363–370, (1993).
Wang et al., "Quantitation Of Endothelial Cell Specific Protein E–9 Employing A Single Monoclonal Antibody In An Indirect Sandwich ELISA", *Journal of Immunological Methods*, vol. 171:55–64, (1994).
Westphal et al., "A New 180–kDa Dermal Endothelial Cell Activation Antigen: In Vitro and In Situ Characteristics", *The Journal of Investigative Dermatology*, vol. 100, No. 1, pp. 27–34, (1993).
Shibuya et al., "Nucleotide Sequence And Expression Of A Novel Human Receptor–Type Tyrosine Kinase Gene (flt) Closely Realted To The fms Family", *Oncogene*, vol. 5:519–524, (1990).

*Primary Examiner*—James H. Reamer
*Attorney, Agent, or Firm*—Foley & Lardner

[57] ABSTRACT

The invention relates to a combination of substances (component I) inducing necrosis in tumors or inflamed tissue with other nontoxic substances ("prodrugs", component II). The enzymes set free by necrotic processes then cleave the nontoxic "prodrug" into the toxic "drug", which leads to massive tumor cell death and/or remission of inflammation.

14 Claims, No Drawings

COMBINATION OF NECROSIS-INDUCING SUBSTANCES WITH SUBSTANCES WHICH ARE ACTIVATED BY NECROSES FOR THE SELECTIVE THERAPY OF TUMORS AND INFLAMMATORY DISORDERS

FIELD OF THE INVENTION

The invention relates to a combination of substances (component I) inducing necrosis in tumors or inflamed tissue, processing with other nontoxic substances ("prodrugs", component II). The enzymes set free by necrotic processes then cleave the nontoxic "prodrug" into the toxic "drug", which leads to massive tumor cell death and/or remission of inflammation.

BACKGROUND OF THE INVENTION

Only chemotherapy is available today for the treatment of advanced (metastasized) solid tumors. This form of therapy does produce a demonstrable antitumor effect in a number of solid tumors but only with usually severe side effects for the patient. From this unsatisfactory situation the urgent need arises to develop better forms of therapy which have low side effects.

In recent years, several attempts were undertaken, based on specific immunological recognition mechanisms, to introduce novel and efficient therapies into the clinic. It is a matter here especially of therapy attempts in which toxic principles are to be transported to the tumor tissue by means of antibodies which are selective for the surface structures on tumors. In these clinical attempts, it turned out that macromolecules, such as e.g. monoclonal antibodies or their recombinant variants, do bind very selectively to the tumor cells in vivo, but only to a very low extent which is usually inadequate for therapy. These scientific results led to the development of so-called multi-step concepts, in which an enzyme was coupled to a tumor-selective monoclonal antibody (antibody-enzyme conjugate), which is able, after an appropriate prelocalization phase on the tumor (1st step), to cleave a nontoxic low-molecular weight prodrug (2nd step) injected afterwards selectively at the tumor site to give a toxic drug. Preclinically this two-phase concept leads to higher drug concentrations on the tumor than conventional chemotherapy, which is accompanied by improved activity in the human tumor xenograft model in the nude mouse (Senter, P. D. et al., Bioconj. Chem. 4:3–9, 1993). In addition to the immunogenicity which is to be expected of the antibody-enzyme conjugates used (mouse antibody bound to xenogenic, usually bacterial enzymes), their problems of penetration through the solid tumor and their restriction to certain tumor types, depending on the presence of the tumor-associated antigen recognized, are to be mentioned. From this the need results to develop various antibody-enzyme conjugates of different specificity in order to be able to treat at least the most frequent tumors (gastrointestinal tract, pulmonary, breast, ovarian and prostate carcinomas).

SUMMARY OF THE INVENTION

It is an object of this invention to provide a pharmaceutical two-component, combination composition, wherein one component of the combination collaborates with a second component in providing low side effect therapy of solid tumors and inflammatory processes.

This object is achieved by a pharmaceutical composition comprising two types of components, hereinafter referred to as components I and II. Component I is a compound that tumor-selectively induces tissue necroses or is selectively toxic for proliferating endothelium as an inflammation, and II is a nontoxic prodrug that is cleaved by enzymes set free during necrotic or inflammatory processes to yield a drug that is cytotoxic to the target tissue.

In a preferred embodiment, component I may be a monoclonal antibody inducing cell destruction and/or apoptosis, an immunoconjugate thereof, a ligand toxin, or a tumor or endothelial cell metabolism inhibiting substance.

Component II may be a nontoxic prodrug that is converted to a tumor or endothelial cell cytotoxic active drug by the action of an enzyme released by Component I.

These and additional objects and aspects will be detailed in the following detailed description of the invention and in the appended claims.

DETAILED DESCRIPTION OF THE INVENTION

In the following a pharmaceutical composition is now presented which surprisingly does not have the problems of immunogenicity, heterogeneity and lack of tumor penetration pointed out above, but has the advantages of the two-phase concept, the improved drug concentration on the tumor, and accordingly makes possible a universally employable low side effect therapy of solid tumors.

The pharmaceutical composition consists of two components, one component which tumor-selectively induces necroses or is selectively toxic for proliferating endothelium (tumor endothelium or endothelium in inflammatory processes) and a nontoxic prodrug component which is cleaved by enzymes set free during necrotic processes to give a toxic drug. The necrosis-inducing component I can be an inhibitor of the tumor or endothelial cell metabolism or a tumor endothelium-specified substance. The tumor endothelium-specific or necrosis-inducing component I is administered parenterally, preferably intravenously.

In the case of the tumor endothelium-specific component, it binds selectively to one epitope which is expressed preferentially on proliferating endothelium of the blood vessels without having to penetrate the tumor interstitium.

After internalization of the component into the proliferating endothelial cells or as a result of activation of cytotoxic host effector mechanisms in the case of non-internalization, the proliferating endothelium is inhibited in its growth or completely destroyed. From this an undersupply of nutrient to numerous tumor cells results, which leads to growth inhibition and to the dying of certain tumor areas. Comparable effects can also be achieved by tumor metabolism- or endothelial metabolism-inhibiting substances which can be injected i.v.. In the necrosis thus formed, intracellular enzymes, preferably lysosomal glycosidases, are released which cleave the component II then preferably to be injected i.v., the nontoxic prodrug, to the toxic drug. The high drug concentrations thus produced in the tumor then lead to massive tumor cell death, to the superior antitumor effect of this new two-component therapy and/or remission of inflammation.

As component I of the novel two-component system, various substances described in greater detail in the following can be used:

a) monoclonal antibodies (MAb), selectively for proliferating endothelium or its humanized variants having complement-activating and/or the "antibody-dependent cell-mediated cytotoxicity" ADCC-mediating Fc part (mode of action by means of cell destruction) and also noncytolytic variants or fragments (induction of apoptosis);

b) immunoconjugates of substances described under a), bound to toxins or toxic chemicals;
c) ligand toxins specific for proliferating endothelium, consisting of a receptor ligand bound to toxins or to toxic chemicals;
d) tumor cell- or endothelial cell metabolism-inhibiting substances, which in each case locally destroy at least parts of tumor cell populations.

The monoclonal antibodies described under a) are preferably specific for a proliferation-dependent endothelial antigen, such as e.g. the VEGF receptor (Terman et al., 1991, Oncogene 6, 1677–1683; Ullrich and Schlesinger, 1990, Cell 61, 203–212; Millauer et al., 1993, Cell 72, 835–845; Millauer et al., 1994, Nature 367 (6463) 576–579; Kaipainen et al., 1993, J. Exp. Med. 178 (6), 2077–2088; Plate et al., 1993, Cancer Res. 53, 5822–5827), the antigens or endothelium described by Clarke and West (Electrophoresis, 12 (7–8), 500–508, 1991), the 30.5 kDa tumor endothelium-specific antigen described by Hagemeier et al. (Int. J. Cancer 38 (4) 481–488, 1986), an apoptosis-mediating antigen occurring on proliferating endothelial cells, such as, for example, the vitronectin receptor (integrin $\alpha_v\beta_3$) (Brooks et al., Science, 264, 569–71, 1994; Brooks et al., Cell 79, 1157–64, 1994), the VEGF/VEGF receptor complex (VEGF/FLK1, VEGF/KDR) (Abraham et al., U.S. Pat. No. 5,219,739, Abraham et al., WO 91 02058A, Millauer et al., Cell 72, 835–846, 1993; Terman et al., Oncogene 6, 1677–1683, 1991, Terman et al., Biochem. Biophys. Res. Comm., 187, 1579–1586, 1992), the fibronectin $CH_2$ domain (Carnemolla et al., J. Cell Biol. 108, 1139–1148, 1989, Castellani et al., Int. J. Cancer, 59, 612–618, 1994), endoglin (Fernandez-Ruiz et al., Cytogenet. Cell Genet. 64, 204–207, 1993; Gougos et al., J. Biol. Chem. 265, 8361–8364, 1990), endosialin (Garin-Chesa and Rettich, U.S. Pat. No. 5,342,757), the antigens defined in WO 94/10331 by means of MAb and occurring on proliferating endothelia, the EAM-1 sialoglycoprotein antigen (EPA 0583 799A), the FLK-2 protein (WO 94/01576), the CMP-170 antigen (EPA 0 585 963 A1), the E9 antigen (Wang et al., Int. J. Cancer 54, 363–370, 1993, Wang et al., J. Immunol. Methods 171, 55–64, 1994), the novel 180 kDa dermal endothelial cell-activation antigen (Westphal et al., J. Invest. Dermatol. 100, 27–34, 1993), the FLt protein (Shibuya et al., Oncogene 5, 519–524, 1990; DeVries et al., Science 255, 989–991, 1992), the PDGF receptor $\beta$ (Plate et al., Laboratory Investigation, 67, 529–534, 1992), the PDGF/PDGF receptor $\beta$-complex, the PDEGF/PDEGF receptor complex (Ishikawa et al., Nature 338, 557–562, 1989), the inducible, blood-brain barrier endothelium-specific antigen HT7 (neurothelin, basignin; gp 42, OX 47) (Seulberger et al., Annals of the New York Academy of Sciences, 633, 611–614, 1991; Seulberger et al., Neuroscience Letter 140, 93–97, 1992). Additionally to the MAb defined above, the MAb mentioned by Burrows and Thorpe (Pharmac. Ther. 64, 155–174, 1994) can also be used. All MAb mentioned in a) can also be used for the preparation of fusion proteins in combination with procoagulating factors (Denekamp, Cancer Topics 6, 6–8, 1986) or cytokines or chemokines (Mulligan, Science 260, 926–932, 1993). Associated with vector DNA, which codes for proinflammatory, immunoregulatory or proliferation-inhibiting proteins, the MAb described under a), which internalize, can especially be used for the "targeting" and for the modification of the proliferating endothelium (Nabel et al., Science 249, 1285–1288, 1990). In principle, an internalization, if not mediated by the antigen recognized itself, can be brought about by the administration of a second antibody having specificity against the first. Instead of classical MAb obtained from hybridomas, antibodies obtained from non-human or human gene banks by means of "display libraries" (Little et al., Biotech Adv. 12, 539–555, 1994) and their derivatives such as e.g. "single chain fragment variable region" (scFvs), "domain antibodies" (dAbs), antigen-binding peptides or peptide mimetics with the above specificities can of course also be used. Antigen-binding peptides are in particular the cyclic peptides mentioned in Brooks et al. (p. 3 loc. cit.) which induce apoptosis by means of binding to the vitronectin receptor. The immunoconjugates described under b) are produced by coupling the specific antibodies or their variants defined under a) with toxins of xenogenic origin (ricin A, diphtheria toxin A, Pseudomonas exotoxin A; Burrows and Thorpe, PNAS 90, 8996–9000, 1993) or human origin (angiogenin, RNAses; Rybak et al., PNAS 89, 3165–3169, 1992). Furthermore, linkage with toxic synthetics or natural substances, such as e.g. alkylating agents, antimetabolites, anthracyclines, Vinca alkaloids, taxol, chalichimycin etc., and radioisotopes, preferably $\alpha$- or $\beta$-emitters in complexed form (e.g.: Y-90 DOTA:2-(p-nitrobenzyl)-1,4,7,10-tetracyclododecane-N,N',N'',N''', N''''-tetraacetic acid; Moi et al., J. Am. Chem. Society, 110, 6266 (1988) can also be carried out.

The ligand toxins described under c) are natural or synthetic ligands which bind to the receptors or antigens defined in a) by means of MAb, preferably variants of the "vascular endothelial growth factor" (VEGF) (Shweiki et al. 1993, J. Clin. Invest. 91, 2235–2243), bound to the toxins and toxic substances described under b), and VEGF antagonists or agonists.

In the case of the tumor cell- or endothelial cell metabolism-inhibiting substances (d), e.g. 5,6-dimethylxanthenone acetic acid or flavoneacetic acid (Zwi et al., Pathology 26, 161–169, 1994), Zilascorb (5,6-O-benzylidene-d-L-ascorbic acid; Pettersen et al., Brit. J. Cancer 67, 650–656, 1993) or AGM 1470 (Antoine et al., Cancer Res. 54, 2073–2076, 1994) can be used. Other examples of tumor cell metabolism-inhibiting substances are immunoconjugates or fusion proteins, these constructs being selective for an internalizable tumor-associated antigen, bound to a toxic component, preferably a metabolism-inhibiting enzyme, e.g. Pseudomonas exotoxin (Brinkmann et al., Proc. Natl. Acad. Sci. USA, 88, 8616–8620, 1991), a toxic synthetic such as cyclophosphamide or toxic natural substance, e.g. daunomycin.

The injection of the respective components I described under a)–d) into a patient thus results in selective tissue necrosis either as a result of direct damage to the tumor tissue (d) or indirectly as a result of affecting the proliferating endothelium (a,b,c).

At the same time as and/or after occurrence of the necrosis, prodrugs which can be cleaved by enzymes which are set free during tumor cell necrosis are injected as component II, for example the prodrugs described in EP-A-0 511 917 A1 or EP-A-0 595 133, preferably the N-(4-$\beta$-glucuronyl-3-nitrobenzyloxycarbonyl)doxorubicin prodrug (called "prodrug" in the examples) described in Bosslet et al. (Cancer Res. 54, 2151–2159, 1994) in FIG. 3.

In the following, animal-experimental examples are described which confirm the superior pharmacodynamic activity of the novel two-component therapy. These animal models have a high predictiveness for the clinical situation.

EXAMPLE 1

The mouse model set up by Burrows and Thorpe (Proc. Natl. Acad. Sci., USA, 90, 8996–9000, 1993) was used to confirm the superior pharmacodynamic activity of an anti-tumor endothelial immunotoxin (component I) together with the prodrug (F 826) as the component II.

The mouse model is set up as follows:

A mixture of 1.4×10⁷ C1300 mouse neuroblastoma cells and 6×10⁶ C1300 Muγ cells (mouse neuroblastoma line transfected with mouse γ-interferon) was injected subcutaneously into the right anterior flank of Balb/c nu/nu mice. Fourteen days later, when the tumors had attained a diameter of 0.8–1.2 cm, the animals were randomized into four groups of 6 animals each. The animals received the immunotoxin on day 15 and the prodrug injected i.v. on days 17, 20 and 23.

The tumor endothelium immunotoxin injected consists of a monoclonal antibody (MAb M 5/114), which is specific for mouse MHC class II molecules of the haplotype d, bound to the deglycosylated ricin A chain. Normal endothelial cells of Balb/$^c$ nu/nu mice do not express any MHC class II molecules. The γ-interferon released locally in vivo by the C1300 Muγ tumor cells leads, however, in the tumor to an activation of the endothelial cells located there, combined with a clear expression of MHC class II molecules. By means of this, a quasi-tumor endothelium-specific antigen is produced (apart from mouse B cells, macrophages and some epithelial cells which constitutively express the MHC class II antigens). The injection of the immunotoxin should accordingly lead to a preferential binding to the tumor endothelial cells, followed by endothelium destruction after internalization of the conjugate. The necrosis resulting from the tumor endothelium destruction leads to a release of intracellular enzymes, but especially β-glucuronidase, which should activate the subsequently administered prodrug in the tumor.

In order to confirm this hypothesis, the experimental animals divided into four groups were treated as described in Table 1.

TABLE 1

| | Treatment scheme | |
|---|---|---|
| Group | Immunotoxin; μg/mouse | Prodrug; mg/mouse |
| 1 | 4 | 4 |
| 2 | 4 | 0 |
| 3 | 0 | 4 |
| 4 | 0 | 0 |

The tumor growth was determined by measuring two diameters of the tumor which are perpendicular to one another by means of a slide gauge on each day of the experiment. The tumor volume was determined with the aid of the formula V=½ ab², a being the largest and b the smallest diameter.

The tumors of experimental group 4 showed progressive growth. As a result of treatment three times with prodrug (group 3) or with immunotoxin (group 2), strong tumor growth-inhibitory effects were achieved. All animals of group 1 were treated into a complete regression. This experiment confirms the superior activity of the novel two-component therapy with immunotoxin and prodrug. Instead of the immunotoxin used here which has specificity for HLA antigens of the mouse (Burrows and Thorpe, PNAS 90, 8996–9000, 1993), the components described under a), b) and c) can be employed in the patient.

EXAMPLE 2

The pharmacodynamic superiority of the novel two-component therapy was confirmed in 2 further independent experiments. Experimental groups in each case containing 6 nude mice were transplanted with the LoVo colon carcinoma or the Mx-1 breast carcinoma. After the tumors had achieved a Φ of ≈5 mm, Zilascorb (Pettersen et al., 1993, Brit. J. Cancer, 67, 650–656; Borretzen et al., U.S. Pat. No. 4,874, 780, 1989) was administered i.v. on days 1–7 and the prodrug F 826 on days 8, 11 and 14. The treatment scheme is described in greater detail in Table 2.

TABLE 2

| | Treatment scheme | |
|---|---|---|
| MX-1 | Zilascorb; mg/mouse | Prodrug; mg/mouse |
| Group 1 | 0.4 | 4 |
| 2 | 0.4 | 0 |
| 3 | 0 | 4 |
| 4 | 0 | 0 |
| LoVo | | |
| Group 1 | 0.8 | 4 |
| 2 | 0.8 | 0 |
| 3 | 0 | 4 |
| 4 | 0 | 0 |

The tumor growth was determined as described in Example 1 and monitored over the course of 30 days after the therapy. The subsequent tumor therapeutic effects were observed:

The experimental groups 4, which were treated with physiological saline solution, showed progressive growth over the treatment period of 38 days. At a tumor diameter of ≧20 mm the animals were sacrificed for ethical reasons. A significant inhibition of tumor growth was to be observed in experimental groups 2 and 3. In more than 50% of the animals of the treatment groups 1 tumor regressions where achieved. These observations show that the novel two-component therapy with Zilascorb and prodrug F 826, in comparison to monotherapy with one of the components, has superior tumor therapeutic activity. In further preclinical in vivo models, in which human pulmonary, breast, prostate, pancreas and gastric carcinomas were used, it was possible to observe effects comparable to those for the MX-1 and the LoVo tumor. Using flavoneacetic acid or 5,6-dimethylxanthenoneacetic acid as the first component, results comparable to those with Zilascorb were obtained. These preclinical in vivo experiments with high predictiveness for the clinical situation show that the novel two-component therapy with tumor cell- or endothelial cell metabolism-inhibiting substances combined with prodrug can be used in a wide range of human tumors of different origin. In the patient, the reagents described under d) would be injected analogously to the animal experiment as component I, followed by F 826 as component II.

EXAMPLE 3

The pharmacodynamic superiority of the novel two-component therapy was confirmed in a further independent experiment. Experimental groups containing 6 animals each were transplanted with the LoVo colon carcinoma. After the tumors has reached a Φ of ≈5 mm, the scFv PE40 construct (Brinkmann, Proc. Natl. Acad. Sci., USA, 88, 8616–8620, 1991) was administered i.v. altogether 4× at 12 hour intervals in each case. The prodrug was administered i.v. on days 3, 6 and 9 after the beginning of the treatment with the ScFv PE40 construct. The treatment scheme is summarized in Table 3.

TABLE 3

| Group | scFv PE40 μg/mouse | Treatment scheme Prodrug; mg/mouse |
|---|---|---|
| 1 | 5 | 4 |
| 2 | 5 | 0 |
| 3 | 0 | 4 |
| 4 | 0 | 0 |

The following experimental result was obtained: in comparison to the control group 4, in the prodrug group 3 only a partial tumor regression was observed, in the case of the ScFv PE40 group 2 only a slowing-down of the tumor growth. In the combination therapy group 1, 4 of 6 animals showed a complete and 2 a partial regression.

This experiment confirms the superior activity of the two-component therapy as exemplified by an immunotoxin which is directed against a tumor-associated antigen (TAA), in combination with prodrug. For administration to the patient, this experiment means that a two-component therapy with the substances described under d), combined with the prodrug F 826, should result in superior tumor therapeutic activity.

In summary it may be observed here that the combination therapy with components I described under a), b), c) and d) and the component II (prodrug) brings about superior tumor therapeutic effects in comparison to monotherapy with the components I or II.

We claim:

1. A pharmaceutical composition for use in cytostatic or immunotherapy, comprising a component I and a component II, wherein said component I comprises at least one compound that produces necroses a in tumor or in an inflammatory process, said necroses resulting in the release of at least one enzyme, and component II comprises one or more compounds that are converted by said at least one enzyme released by said necroses into a cytotoxic drug.

2. A composition according to claim 1, wherein said component I comprises at least one substance selected from the group consisting of a cytolytic or apoptotic monoclonal antibody, an immunoconjugate, a receptor ligand toxin specific for proliferating endothelium, and a tumor cell or endothelial cell metabolism inhibitor substance.

3. A composition according to claim 1, wherein said component I comprises at least one monoclonal antibody or one receptor ligand that is specific for proliferating endothelium.

4. A composition according to claim 3, wherein said receptor-ligand is specific for the VEGF/VEGF receptor complex.

5. A composition according to claim 1, wherein said component I comprises at least one monoclonal antibody, receptor ligand or an antagonist against an apoptosis-mediating antigen occurring on proliferating endothelial cells.

6. A composition according to claim 5, wherein said antigen comprises the $\alpha_v\beta_3$ integrin.

7. A composition according to claim 1, wherein said component I comprises at least one cytotoxic immunoconjugate.

8. A composition according to claim 1, wherein said component I comprises at least one ligand receptor toxin.

9. A composition according to claim 1, wherein said component I comprises at least one tumor cell or endothelial cell metabolism inhibiting substance.

10. A composition according to claim 1, wherein said component II comprises a prodrug.

11. A composition according to claim 10, wherein said prodrug is N-(4-β-glucuronyl-3-nitrobenzylcarbonyl) doxorubicin.

12. A process for treating a subject bearing a solid tumor or inflammatory process, comprising administering to said subject an effective amount of a composition of claim 1 in a suitable pharmaceutical vehicle.

13. A pharmaceutical composition comprising a first component and a second component, said first component comprising a tissue necrosis factor and a second component comprising a prodrug activated by a product of the action of said first component, said first component consisting of a monoclonal antibody specific for the VEGF/VEGF receptor complex, and said second component consisting of N-(4-β-glucuronyl-3-nitrobenzylcarbonyl) doxorubicin.

14. A method of tumoristatic or immunoregulatory therapy in a patient requiring same, comprising the steps of administering to said patient an effective amount of the composition according to claim 13 for an effective period of time.

* * * * *